United States Patent
Bencini et al.

(10) Patent No.: US 8,598,388 B2
(45) Date of Patent: Dec. 3, 2013

(54) PROCESS FOR THE PREPARATION OF PHENOL AND CYCLOHEXANONE

(75) Inventors: Elena Bencini, Virgilio (IT); Cristian Gambarotti, Cremona (IT); Lucio Melone, Montefusco (IT); Nadia Pastori, Rho (IT); Simona Prosperini, Santhià (IT); Carlo Punta, Milan (IT); Francesco Recupero, Milan (IT)

(73) Assignee: Polimeri Europa S.p.A., San Donato Milanese (IT)

( * ) Notice: Subject to any disclaimer, the term of this patent is extended or adjusted under 35 U.S.C. 154(b) by 0 days.

(21) Appl. No.: 13/381,466

(22) PCT Filed: Jun. 23, 2010

(86) PCT No.: PCT/IB2010/001540
§ 371 (c)(1),
(2), (4) Date: Mar. 9, 2012

(87) PCT Pub. No.: WO2011/001244
PCT Pub. Date: Jan. 6, 2011

(65) Prior Publication Data
US 2012/0157718 A1    Jun. 21, 2012

(30) Foreign Application Priority Data
Jun. 29, 2009   (IT) .............................. MI2009A1145

(51) Int. Cl.
*C07C 45/53*  (2006.01)
*C07C 27/00*  (2006.01)

(52) U.S. Cl.
USPC ........................................ 568/342; 568/768

(58) Field of Classification Search
USPC ................................. 568/342, 768
See application file for complete search history.

(56) References Cited

U.S. PATENT DOCUMENTS

| 4,206,082 | A | 6/1980 | Murtha et al. | |
| 4,463,207 | A | 7/1984 | Johnson | |
| 6,037,513 | A | 3/2000 | Chang et al. | |
| 6,720,462 | B2 * | 4/2004 | Kuhnle et al. | 568/768 |
| 6,974,788 | B2 * | 12/2005 | Harris et al. | 502/79 |
| 2006/0258893 | A1 * | 11/2006 | Bencini et al. | 585/475 |
| 2010/0179351 | A1 | 7/2010 | Chen et al. | |

FOREIGN PATENT DOCUMENTS

| WO | 2004 056475 | 7/2004 |
| WO | 2009 038900 | 3/2009 |

OTHER PUBLICATIONS

International Search Report Issued Sep. 24, 2010 in PCT/IB10/001540 Filed Jun. 23, 2010.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

Process for the preparation of phenol and cyclohexanone which comprises:
a. the synthesis of cyclohexylbenzene by the hydro-alkylation of benzene by contact with hydrogen or the alkylation of benzene with cyclohexene using Y zeolites;
b. the selective aerobic oxidation of cyclohexylbenzene to the corresponding hydroperoxide catalyzed by N-hydroxy-derivatives in the presence of polar solvents; and
c. the scission of the hydroperoxide of cyclohexylbenzene to phenol and cyclohexanone by homogeneous or heterogeneous acid catalysts;

characterized in that the synthesis of cyclohexylbenzene takes place in the presence of a catalytic system comprising a Y zeolite and an inorganic ligand wherein the Y zeolite has a crystalline structure with openings consisting of 12 tetrahedra and the inorganic ligand is γ-alumina, and wherein said catalytic composition is characterized by a pore volume, obtained by adding the mesoporosity and macroporosity fractions, greater than or equal to 0.7 cm$^3$/g, wherein at least 30% of said volume consists of pores with a diameter greater than 100 nanometers.

30 Claims, No Drawings

PROCESS FOR THE PREPARATION OF PHENOL AND CYCLOHEXANONE

FIELD OF THE INVENTION

The present invention relates to a process for the preparation of phenol and cyclohexanone.

More specifically, the present invention relates to a process for the preparation of cyclohexylbenzene and its transformation to phenol and cyclohexanone.

Cyclohexylbenzene is prepared by contact between benzene and hydrogen under hydro-alkylation conditions or by the alkylation of benzene with cyclohexene. Both processes are mediated by new catalysts described and claimed herein for this purpose. The cyclohexylbenzene is converted to the corresponding hydroperoxide by selective aerobic oxidation under mild conditions in the presence of a specific catalytic system. The hydroperoxide is then transformed to phenol and cyclohexanone in a process catalyzed by acids.

ART PRIOR TO THE INVENTION

The industrial production of phenol is based on the Hock process, which involves the autoxidation of cumene to the corresponding hydroperoxide and its subsequent acid-catalyzed decomposition to phenol and acetone. (Ullman's Encyclopedia of Industrial Organic Chemicals, Vol. A9, 1958, 225, Wiley-VCH).

The most complex phase which most widely influences the whole process is the autoxidation, in which the hydroperoxide formed acts as initiator of the radical chain by decomposition to cumyloxyl radical. The latter can form cumyl alcohol by the hydrogen abstraction from cumene or undergo β-scission giving acetophenone and methyl radical. These aspects create various drawbacks which influence the whole process. The selectivity in the formation of the hydroperoxide decreases to the same extent to which the hydroperoxide itself acts as initiator. On the other hand, the decomposition of the hydroperoxide increases with the conversion and temperature. A high conversion causes a higher concentration of hydroperoxide and therefore a greater decomposition and lower selectivity. Furthermore, the methyl radical, formed in the β-scission of the cumyloxyl radical, is oxidized under the reaction conditions to formic acid. The latter catalyzes the decomposition of the hydroperoxide to phenol, which inhibits the oxidation process. In industrial processes, the presence of formic acid therefore creates the necessity of operating in the presence of a base, to neutralize the carboxylic acid. This problem also arises in the oxidation of other alkyl aromatic derivatives, for example in the oxidation of sec-butylbenzene in which significant quantities of acetic acid are formed (PCT/US2008/079150).

In order to eliminate or reduce these disadvantages, various expedients have been taken into consideration, such as the use of suitable metallic complexes as catalysts or co-catalysts, which increase the conversion rate and allow to work at lower temperatures at which the hydroperoxide is more stable (Ishii, Y. at al. J. Mol. Catalysis A, 1987, 117, 123). The higher thermal stability of the hydroperoxides at low temperatures, however, is negatively balanced by the redox decomposition caused by the metal salts. These catalytic systems have consequently proved to be inadequate for the preparation of hydroperoxides whereas they are of great industrial interest for the preparation of other oxygenated products (alcohols, aldehydes, ketones, carboxylic acids).

New catalytic systems have recently been proposed for the aerobic oxidation of cumene and other alkylbenzenes, based on the use of N-hydroxyimides and N-hydroxysulfamides associated with radical initiators, such as peroxides and azo-derivatives which operate without metal salts (Ishii, Y. at al. Adv. Synth. Catal. 2001, 343, 809 and 2004, 346, 199; Sheldon, R. A. at al. Adv. Synth. Catal. 2004, 346, 1051; Levin, D. at al. WO 2007/073916 A1; U.S. Pat. Nos. 6,852,893; 6,720, 462). N-hydroxyphthalimide, which can be easily obtained from low-cost industrial products (phthalic anhydride and hydroxyl amine) is of particular interest (Minisci, F. et al. J. Mol. Catal. A, 2003, 63, 204 and 2006, 251, 129; Recupero, F. and Punta C., Chem. Rev. 2007, 107, 3800-3842).

In the presence of N-hydroxyphthalimide (NHPI), aldehydes have proved to have a considerable activity for the production of hydroperoxide of alkyl aromatic compounds under mild aerobic conditions, with a high conversion and selectivity. (Minisci et al. PCT/EP07/008341; Minisci et al. MI2008A000460).

The use of N-hydroxy-derivatives has definite advantages with respect to non-catalyzed autoxidations, but also various disadvantages deriving from the decomposition of the initiators.

The Applicants have recently found that N-hydroxyphthalimide can catalyze the peroxidation of alkyl aromatic compounds under mild conditions if the aerobic oxidation is carried out in the presence of a moderate quantity of polar solvents (ketones, nitriles, esters, dialkyl carbonates and tertiary alcohols) which are completely stable under the operative conditions (Minisci et al. MI2008A000461). The polar solvent has a key function in favouring the dissolution of the organic catalyst, otherwise essentially insoluble under the operative conditions necessary for guaranteeing a high selectivity to hydroperoxide (temperature preferably lower than 110° C.). Under the same operating conditions, in the absence of N-hydroxy-derivative, there is no significant reaction.

The selectivity of this process to hydroperoxide is extremely high. The catalyst remains unaltered and can be easily recovered at the end of the reaction by means of crystallization and/or extraction with water or adsorption on various substrates.

In the peroxidation of cumene, acetone is the most advantageous among polar solvents as it is obtained as co-product during the acid decomposition of the hydroperoxide to phenol.

The demand for phenol, however, is constantly growing with respect to that for acetone. There is consequently a growing interest in processes for the production of phenol which avoid the formation of acetone.

The peroxidation of sec-butylbenzene is interesting as the cost of propylene, with respect to that of butenes, is continuously increasing and the offer is lower than the market request.

Cyclohexylbenzene is even more interesting. It has also been possible to carry out the peroxidation process on this derivative with the method object of the present invention. The corresponding cyclohexanone, obtained together with phenol, is of great industrial interest for the production of caprolactone (precursor of nylon 6) and adipic acid. Furthermore, the possibility of converting phenol to cyclohexanone by hydrogenation, and cyclohexanone to phenol by dehydrogenation (Sheldon et al. Tetrahedron 2002, page 9055) allows the production to be programmed on the basis of the variation in the market requests for the two products.

It is known that cyclohexylbenzene can be produced by reacting benzene with hydrogen in the presence of a catalyst based on ruthenium and nickel supported on beta zeolite (U.S. Pat. No. 5,053,571); or in the presence of carbon monoxide and X or Y zeolites containing palladium (U.S. Pat. No.

5,146,024); or in the presence of a bifunctional catalyst which includes a molecular sieve of the MCM-22 family and a metallic catalyst selected from palladium, ruthenium, nickel, cobalt or a mixture of these (U.S. Pat. No. 6,037,513).

More recently, it has been found that the efficiency of the bifunctional catalyst described above is increased by supporting the metal on an organic oxide, used in the form of a composite with molecular sieves. This catalyst leads to a greater selectivity to mono- and di-cyclohexylbenzene, reducing the formation of cyclohexane (PCT/EP2008/006072).

An alternative method for the preparation of cyclohexylbenzene is the Friedel-Crafts reaction between benzene and cyclohexene. These types of processes are being more and more frequently carried out by means of heterogeneous acid catalysis, preferably based on zeolites.

The Applicants have recently developed an innovative Y zeolite, belonging to the group of large-porosity zeolites, which includes γ-alumina as inorganic ligand (Bencini et al. Patent application U.S.A. 2006/0258893 A1).

This catalyst has proved to be particularly effective in the transalkylation of polyalkylated aromatic hydrocarbons, under such operative conditions that the reaction takes place at least partially in liquid phase.

The present invention relates to the application of this catalyst system to the alkylation reaction of benzene with cyclohexene and, in the presence of a hydrogenating metal, to the hydro-alkylation reaction of benzene by contact with hydrogen.

DESCRIPTION OF THE INVENTION

The object of the present invention, better described in the enclosed claims, therefore relates to: 1) the preparation of cyclohexylbenzene by the hydro-alkylation of benzene by contact with hydrogen or alkylation of benzene with cyclohexene using innovative Y zeolites as catalysts; 2) the selective aerobic oxidation of cyclohexylbenzene to the corresponding hydroperoxide catalyzed by N-hydroxy-derivatives in the presence of polar solvents; 3) the scission of the hydroperoxide of cyclohexylbenzene to phenol and cyclohexanone by means of homogeneous or heterogeneous acid catalysts;

Preparation of Cyclohexylbenzene

The cyclohexylbenzene is prepared according to two different methods. The first method comprises the alkylation reaction of benzene with cyclohexene in the presence of a catalyst based on Y zeolite prepared as described in US patent 2006/0258893.

The feeding mixture consisting of benzene and cyclohexene, before being introduced into the reactor, is treated with adequate dehydrating agents, for example alumina, to reduce the quantity of water contained therein to below 100 ppm, for example below 50 ppm.

The reaction temperature does not exceed 220° C. and preferably ranges from 120 to 180° C., for example 150° C. The operating pressure ranges from 25 to 50 bar, for example 37 bar. The space velocity, expressed as LHSV (Liquid Hourly Space Velocity), ranges from 0.5 to 4 hours$^{-1}$, for example 2 hours$^{-1}$. In order to maximize the yield to mono-alkylated product, an excess of benzene is used, with benzene/cyclohexene molar ratios ranging from 5 to 30, for example equal to 10.

The reaction conditions guarantee an almost total conversion of cyclohexene, with a high selectivity to the mono-alkylation product of benzene. Any possible polyalkylation products can be easily recycled by transalkylation in the presence of the same catalyst.

Alternatively, the cyclohexylbenzene is prepared by contact between benzene and hydrogen in the presence of a hydro-alkylating catalyst based on Y zeolite, prepared as described in US patent 2006/0258893, and containing a percentage of supported metal according to impregnation techniques known in literature (for example those indicated in U.S. Pat. No. 5,146,024). The percentage of metal ranges from 0.05 to 1.5% by weight, preferably from 0.2 to 0.5%, and is equal for example to 0.3% by weight. The metal can be selected from palladium, platinum, nickel, ruthenium, palladium being preferred.

The reaction temperature does not exceed 300° C., and preferably ranges from 120 to 200° C., for example 130° C. The operating pressure ranges from 10 to 30 bar, for example 15 bar. The space velocity, expressed as WHSV (Weight Hourly Space Velocity), ranges from 1 to 4 hours$^{-1}$, for example 2 hours$^{-1}$. The hydrogen/benzene molar ratio ranges from 0.1:1 to 10:1, preferably from 0.5:1 to 5:1, for example 1:1.

The reaction conditions guarantee a good conversion of benzene, with a high selectivity to the hydro-mono-alkylation product.

Oxidation of Cyclohexylbenzene

The cyclohexylbenzene, prepared according to one of the two procedures described above, is converted to the corresponding hydroperoxide by aerobic oxidation in the presence of a catalytic system, which includes N-hydroxyimides or N-hydroxysulfamides, preferably N-hydroxyphthalimides, for example N-hydroxyphthalimide associated with a polar solvent. The temperature does not exceed 130° C., and ranges for example from 50 to 110° C., preferably from 80 to 100° C. The polar solvent can be a $C_3$-$C_{10}$ acyclic or cyclic ketone (for example acetone, methylethylketone, 2-pentanone, 3-pentanone, methyl-t-butylketone, cyclopentanone), also the same cyclohexanone coming from the acid decomposition of the hydroperoxide, or other solvents such as nitriles, esters, tertiary alcohols, dialkylcarbonates, also stable under the reaction conditions.

The quantity of N-hydroxy-derivative catalyst ranges from 0.1 to 10% in moles, for example from 0.5 to 5%, preferably from 1 to 2% in moles.

The ratio between the volume of polar solvent with respect to the volume of alkylbenzene preferably varies within the range of 5:1 to 1:20.

The reaction is carried out with oxygen or air or mixtures of $N_2/O_2$ having a ratio between $N_2$ and $O_2$ ranging from 10:1 to 1:10, operating at pressures ranging from 1 to 20 bar.

At the end of the reaction, the N-hydroxy-derivative, in particular the more convenient N-hydroxyphthalimide, is for the most part recovered by crystallization from the reaction mixture from which the polar solvent has been removed by distillation. The small quantity of residual catalyst can be recovered by extraction with water or adsorption on various substrates from the reaction mixture.

Under the same operating conditions, in the absence of N-hydroxyphthalimide, the reaction does not take place to a significant degree.

Scission of the Hydroperoxide of Cyclohexylbenzene to Phenol and Cyclohexanone

The hydroperoxide of cyclohexylbenzene, obtained in the oxidation phase of cyclohexylbenzene according to the procedure described above, is finally transformed to phenol and cyclohexanone by contact with an acid catalyst in homogeneous and heterogeneous phase.

After removing the polar solvent used in the oxidation reaction, and after recovering the catalyst, the reaction mixture is introduced into the scission reactor, preferably at a concentration of hydroperoxide obtained in the oxidation process, ranging for example from 20 to 30%. Alternatively, the oxidation reaction mixture can be concentrated to up to 80% of hydroperoxide before being introduced into the scission reactor, by removal of the cyclohexylbenzene at reduced pressure. Alternatively, the oxidation reaction mixture can be diluted with inert solvent which favours the removal of the heat developed.

The scission reaction can be carried out in a distillation unit. The process is carried out at a temperature ranging from 0 to 150° C., preferably from 20 to 90° C. The pressure preferably ranges from 1 to 20 bar.

Protic acids can be used as homogeneous catalysts (for example sulphuric acid, phosphoric acid, chloride acid, p-toluenesulfonic acid) or Lewis acids (for example ferric chloride, zinc chloride, boron trifluoride). Acid zeolites such as, for example, beta zeolites, zeolites Y, X, ZSM-5, ZSM-12 or mordenite, can be used as heterogeneous catalysts.

The mixture deriving from the scission is subjected to distillation to recover cyclohexanone, phenol and non-reacted cyclohexylbenzene.

The phenol can be converted to cyclohexanone by hydrogenation and the cyclohexanone to phenol by dehydrogenation.

The following examples are provided for illustrative but non-limiting purposes for the process of the present invention.

EXAMPLE 1

For the alkylation of benzene with cyclohexene, the catalyst based on Y zeolite prepared as described in Example 1 of Patent Application USA 2006/0258893, is used as alkylation catalyst. The reactor used for the catalytic test is of the Berty type, consisting of a reaction chamber having a capacity of 250 cm$^3$ inside which there is a 50 cm$^3$ drum into which the above catalyst is charged. The head of the reactor is situated in the upper part of the reaction chamber, and supports a rotor which rotates by means of a magnetic joint. The reactor is equipped with a temperature and pressure regulation system. Before being introduced into the reactor, the feeding mixture is passed through an alumina column to reduce the quantity of water contained therein to below 50 ppm and is then fed in continuous to the reactor. The conditions under which the test is carried out are the following: reaction temperature equal to 150° C., reaction pressure equal to 37 bar, space velocity expressed as LHSV equal to 2 hours$^{-1}$, benzene/cyclohexene molar ratio equal to 10. The effluent from the reactor is collected in a tank and analyzed by means of gaschromatography using an HP 5890 Series 2 instrument equipped with a capillary column with a Carbovax 20M stationary phase and a detector of the flame ionization type (FID).

Under the above reaction conditions, a conversion of cyclohexene of 99.6% is obtained, with a selectivity to cyclohexylbenzene of 87.7% and a selectivity to useful aromatic compounds (intended as the sum of the desired product cyclohexylbenzene and dicylcohexylbenzenes which can be recovered by transalkylation) of 98.3%.

EXAMPLE 2

For the hydro-alkylation of benzene, the catalyst based on Y zeolite prepared as described in Example 1 of Patent Application USA 2006/0258893 and containing 0.3% of palladium supported according to impregnation techniques known in literature, is used as catalyst. The experimental device used is the same as that described in Example 1. The conditions under which the test is carried out, after activation of the metal by pretreatment with hydrogen, are the following: reaction temperature equal to 120° C., reaction pressure equal to 15 bar, space velocity expressed as WHSV equal to 2 hours$^{-1}$, hydrogen/benzene molar ratio 1:1. The effluent from the reactor is collected in a tank and analyzed by means of gaschromatography using an HP 5890 Series 2 instrument equipped with a capillary column with a Carbovax 20M stationary phase and a detector of the flame ionization type (FID).

Under the above reaction conditions, a conversion of benzene equal to 52.5% is obtained, with a selectivity to cyclohexylbenzene of 41.6%.

EXAMPLE 3

A solution consisting of 5 mL of cyclohexylbenzene (29.4 mmoles) prepared as described in Examples 1 or 2, 1.90 mL of acetonitrile and 0.29 mmoles of N-hydroxyphthalimide is stirred at 70° C. for 24 hours in an oxygen atmosphere at a pressure of 1 bar. $^1$H-NMR analysis of the reaction mixture indicated a conversion of cyclohexylbenzene equal to 28% with a selectivity to cyclohexylbenzene hydroperoxide of 99% (result confirmed by iodometric titration, GC-MS analysis in the presence of an internal standard after reduction of the hydroperoxide to the corresponding alcohol with PPh$_3$ and HPLC analysis of the reaction mixture without any treatment). There was no decomposition of the N-hydroxyphthalimide. The acetonitrile is removed by distillation and 0.52 mmoles of N-hydroxyphthalimide are recovered.

EXAMPLE 4

The same procedure is adopted as described in Example 3, using 2-pentanone at 100° C. instead of acetonitrile, leaving the mixture to react for 6 hours. $^1$H-NMR analysis of the reaction mixture indicated a conversion of cyclohexylbenzene equal to 35% with a selectivity to cumyl hydroperoxide of 99% (result confirmed by iodometric titration and HPLC analysis with an internal standard). 0.51 mmoles of N-hydroxyphthalimide are recovered.

EXAMPLE 5

The same procedure is adopted as described in Example 3, using propionitrile at 100° C. instead of acetonitrile, leaving the mixture to react for 6 hours. $^1$H-NMR analysis of the reaction mixture indicated a conversion of cyclohexylbenzene equal to 36% with a selectivity to cumyl hydroperoxide of 99% (result confirmed by iodometric titration and HPLC analysis with an internal standard). 0.51 mmoles of N-hydroxyphthalimide are recovered.

EXAMPLE 6—COMPARATIVE

The same procedure is adopted as described in Example 4, without N-hydroxyphthalimide. There is no significant conversion of cyclohexylbenzene after 6 hours. After 24 hours, the conversion is high, but the selectivity to hydroperoxide decreases drastically, due to the decomposition of the hydroperoxide.

EXAMPLE 7—COMPARATIVE

The same procedure is adopted as described in Example 3, without acetonitrile. The conversion of cyclohexylbenzene is <1%.

EXAMPLE 8—COMPARATIVE

The same procedure is adopted as described in Example 4, without 2 pentanone. The conversion of cyclohexylbenzene after 6 hours is <10%.

The invention claimed is:

1. A process for preparing phenol and cyclohexanone, the process comprising:
   (a) hydro-alkylating benzene with hydrogen or alkylating benzene with cyclohexene in the presence of at least one Y zeolite to form cyclohexylbenzene;
   (b) selective aerobic oxidation of the cyclohexylbenzene to form a hydroperoxide, wherein the oxidation is catalyzed by at least one N-hydroxy-derivative in the presence of at least one polar solvent; and
   (c) scission of the hydroperoxide to form phenol and cyclohexanone, wherein the scission is catalyzed by at least one homogeneous or heterogeneous acid catalyst,
   wherein
   the hydro-alkylating or alkylating (a) occurs in the presence of a catalytic composition comprising the Y zeolite and an inorganic ligand,
   the Y zeolite has a crystalline structure with openings consisting of 12 tetrahedra,
   the inorganic ligand is γ-alumina,
   the catalytic composition has a pore volume, calculated by summing the mesoporosity and macroporosity fractions, of greater than or equal to 0.7 cm$^3$/g, and
   at least 30% of the pore volume consists of pores with a diameter greater than 100 nanometers.

2. The process of claim 1, wherein the catalytic composition has an apparent density lower than 0.5 cm$^3$/g.

3. The process of claim 1, wherein the catalytic composition is in the form of particles having a diameter larger than 1.8 mm.

4. The process of claim 1, wherein a feeding mixture is pretreated with at least one dehydrating agent to reduce the quantity of water to below 100 ppm, prior to the hydro-alkylating or the alkylating (a).

5. The process of claim 1, comprising alkylating (a) benzene with cyclohexene at a temperature ranging from 120 to 180° C.

6. The process of claim 5, wherein the alkylating (a) of benzene occurs at a pressure ranging from 25 to 50 bar.

7. The process of claim 5, wherein the alkylating (a) of benzene occurs at a space velocity ranging from 0.5 to 4 hours$^{-1}$.

8. The process of claim 5, wherein the alkylating (a) of benzene occurs with a benzene/cyclohexene ratio ranging from 5 to 30.

9. The process of claim 1, comprising hydro-alkylating (a) benzene with hydrogen with a hydrogen/benzene molar ratio ranging from 0.1:1 to 10:1.

10. The process of claim 9, wherein the catalytic composition further comprises a supported metal in a percentage ranging from 0.05 to 1.5% by weight.

11. The process of claim 9, wherein the catalytic composition is pretreated with hydrogen.

12. The process of claim 10, wherein the supported metal is selected from the group consisting of palladium, platinum, nickel, ruthenium.

13. The process of claim 9, wherein the hydro-alkylating (a) is carried out at a temperature ranging from 120 to 200° C.

14. The process of claim 9, wherein the hydro-alkylating (a) is carried out at a pressure ranging from 10 to 30 bar.

15. The process of claim 9, wherein the hydro-alkylating (a) is carried out at a space velocity, ranging from 1 to 4 hours$^{-1}$.

16. The process of claim 4, wherein the feeding mixture comprises dicyclohexylbenzene which is contacted with benzene under transalkylation conditions to produce further cyclohexylbenzene.

17. The process of claim 1, wherein the oxidation (b) is carried out in the presence of
   oxygen,
   a catalytic system comprising the at least one N-hydroxy-derivative selected from the group consisting of an N-hydroxyimide and an N-hydroxysulfamide, and
   the at least one polar solvent.

18. The process of claim 17, wherein the at least one N-hydroxy-derivative is selected from the group consisting of N-hydroxyphthalimide and N-hydroxysaccharin.

19. The process of claim 1, wherein the oxidation (b) is carried out at a temperature lower than 130° C.

20. The process of claim 1, wherein the oxidation (b) is carried out with oxygen, air or mixtures of $N_2/O_2$ having a ratio between $N_2$ and $O_2$ ranging from 10:1 to 1:10, at a pressure ranging from 1 to 20 bar.

21. The process of claim 1, wherein the oxidation (b) is carried out in the presence of the at least one polar solvent selected from the group consisting of a ketone, a nitrile, an ester, a tertiary alcohol, and a dialkyl carbonate.

22. The process of claim 1, wherein the oxidation (b) is carried out with a quantity of the at least one N-hydroxy-derivative ranging from 0.1 to 10% in moles, with respect to the cyclohexylbenzene.

23. The process of claim 1, wherein the oxidation (b) is carried out with a ratio between the volume of the at least one polar solvent, with respect to a volume of cyclohexylbenzene, ranging from 5:1 to 1:20.

24. The process of claim 1, wherein the at least one acid catalyst is selected from the group consisting of a protic acid and a Lewis acid.

25. The process of claim 24, wherein the at least one catalyst is selected from the group consisting of sulfuric acid, phosphoric acid, chloride acid, p-toluenesulfonic acid, Amberlyst, ferric chloride, zinc chloride, and boron trifluoride.

26. The process of claim 24, wherein the at least one acid catalyst is selected from the group consisting of beta zeolite, Y zeolite, X zeolite, ZSM-5 zeolite, ZSM-12 zeolite and mordenite.

27. The process of claim 1, wherein the scission (c) is carried out at a temperature ranging from 0 to 150° C.

28. The process of claim 1, wherein the scission (c) is carried out at a pressure ranging from 1 to 20 bar.

29. The process of claim 1, wherein the cyclohexylbenzene is formed by alkylating benzene with cyclohexene.

30. The process of claim 1, wherein the cyclohexylbenzene is formed by hydro-alkylating benzene with hydrogen and cyclohexene.

* * * * *